United States Patent
Huo et al.

(10) Patent No.: US 10,113,160 B2
(45) Date of Patent: Oct. 30, 2018

(54) CARBON DIOXIDE FIXATION VIA BYPASSING FEEDBACK REGULATION

(71) Applicant: Easel Biotechnologies, LLC, Culver City, CA (US)

(72) Inventors: Yi-Xin Huo, Los Angeles, CA (US); Benjamin Schilling, Sacramento, CA (US); Shahrooz Rabizadeh, Los Angeles, CA (US)

(73) Assignee: Easel Biotechnologies, LLC, Culver City, CA (US)

( * ) Notice: Subject to any disclaimer, the term of this patent is extended or adjusted under 35 U.S.C. 154(b) by 61 days.

(21) Appl. No.: 15/115,670

(22) PCT Filed: Jan. 30, 2015

(86) PCT No.: PCT/US2015/013947
§ 371 (c)(1),
(2) Date: Jul. 30, 2016

(87) PCT Pub. No.: WO2015/117019
PCT Pub. Date: Aug. 6, 2015

(65) Prior Publication Data
US 2016/0348086 A1 Dec. 1, 2016

Related U.S. Application Data

(60) Provisional application No. 61/933,422, filed on Jan. 30, 2014.

(51) Int. Cl.
*C12P 7/16* (2006.01)
*C12P 7/62* (2006.01)
(Continued)

(52) U.S. Cl.
CPC .............. *C12N 9/88* (2013.01); *C10L 1/00* (2013.01); *C12N 9/1205* (2013.01); *C12N 15/74* (2013.01);
(Continued)

(58) Field of Classification Search
None
See application file for complete search history.

(56) References Cited

U.S. PATENT DOCUMENTS

2010/0068776 A1* 3/2010 Woods ............... C12N 15/74
435/161
2011/0008861 A1* 1/2011 Berry ................... C12N 1/20
435/161
(Continued)

FOREIGN PATENT DOCUMENTS

WO 2009098089 A2 8/2009

OTHER PUBLICATIONS

Christian Fleige et al: "Establishment of an alternative phosphoketolase-dependent pathway for fructose catabolism inH16", Applied Microbiology and Biotechnology, vol. 91. No. 3, Apr. 26, 2011, pp. 769-776.
(Continued)

*Primary Examiner* — Richard C Ekstrom
(74) *Attorney, Agent, or Firm* — Lucas & Mercanti LLP

(57) ABSTRACT

Genetically engineered cells and methods are presented that allow for the production of various value products from $CO_2$. Contemplated cells have a CBB cycle that is genetically modified such that two molecules of $CO_2$ fixed in the CBB cycle can be withdrawn from the modified CBB cycle as a single C2 compound. In contemplated aspects a CBB cycle includes an enzymatic activity that generates the single C2 compound from a compound of the CBB cycle, while further modifications to the CBB cycle will not introduce additional recombinant enzymatic activity/activities outside the already existing catalytic activities in the CBB cycle.

11 Claims, 4 Drawing Sheets

(51) Int. Cl.
- C12P 5/02 (2006.01)
- C12N 9/88 (2006.01)
- C12N 9/12 (2006.01)
- C10L 1/00 (2006.01)
- C12N 15/74 (2006.01)

(52) U.S. Cl.
CPC ............... C12P 7/16 (2013.01); C12P 7/625 (2013.01); C12Y 207/01019 (2013.01); C12Y 401/02009 (2013.01); *C10L 2200/0469* (2013.01); *C10L 2290/26* (2013.01); *C12P 5/026* (2013.01); *Y02E 50/10* (2013.01)

(56) References Cited

U.S. PATENT DOCUMENTS

| | | |
|---|---|---|
| 2012/0142066 A1 | 6/2012 | Baier et al. |
| 2013/0252300 A1 | 9/2013 | Green et al. |

OTHER PUBLICATIONS

Victor Guadalupe-Medina et al: "Carbon dioxide fixation by Calvin-Cycle enzymes improves ethanol yield in yeast", Biotechnology for Biofuels, vol. 6. No. 1, Aug. 29, 2013, p. 125.

Zhuang Zong-Yu et al: "Rubisco-based engineered *Escherichia coli* for in situ carbon dioxide recycling", Bioresource Technology, vol. 150, Oct. 3, 2013, pp. 79-88.

Bowien B et al: "Genetics and control of CO2 assimilation in the chemoautotroph Ralstonia eutropha", Archives of Microbiology, vol. 178, Jun. 14, 2002, pp. 85-93.

European Search Report issued for corresponding European Appln No. EP15743189.1 dated Jun. 7, 2017 (5 pages).

Knoop, Fl, et al., "Flux Balance Analysis of Cyanobacterial Metabolism: The Metabolic Network of *Synechocystis* sp. PCC 6803," PLOS Computational Biology 9(6): Jun. 2013, pp. 1-15.

Grzeszik, C., et al., "Phosphoenolpyruvate as a Signal Metabolite in Transcriptional Control of the cbb CO2 Fixation Operons in Ralstonia eutropha," J. Mol. Microbiol. Biotechnol. (2000) vol. 2(3): pp. 311-320.

Bogorad, I.W., et al. "Synthetic non-oxidative glycolysis enables complete carbon conservation," Nature, Jan. 2013, vol. 000, pp. 1-6.

Bogorad, I.W., et al. "Synthetic non-oxidative glycolysis enables complete carbon conservation," Nature, Jan. 2013, vol. 000, pp. 1-19, Supplementary Information.

Wang, X., et al., "Reversible inactivation and characterization of purified inactivated form 1 ribulose 1,5-biphosphate carboxylase/oxygenase of Rhodobacter sphaeroides," J. Bacteriol. 1992, 174(11):3593.

Wang, X., et al., "Reversible inactivation and characterization of purified inactivated form 1 ribulose 1,5-biphosphate carboxylase/oxygenase of Rhodobacter sphaeroides," J. Bacterial. 1992, 174(11):3601.

* cited by examiner

N-rich: ammonium concentration higher than 10 mM.
N-low: ammonium concentration around 3 mM (concentration in continuous run).
N-depletion: ammonium concentration less than 1 mM (best iBOH production phase).

CARBON DIOXIDE FIXATION VIA BYPASSING FEEDBACK REGULATION

This application claims priority to US provisional application having Ser. No. 61/933,422, which was filed Jan. 30, 2014, and is incorporated by reference herein.

FIELD OF THE INVENTION

The field of the invention is biological fixation of carbon dioxide, particularly using genetically modified microorganisms.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Carbon fixation is commonly performed by autotrophic plants and microorganisms such as chemoautotrophic and phototrophic microorganisms by incorporation of $CO_2$ into more complex molecules, typically via the CBB cycle (Calvin-Benson-Bassham cycle, also known as reductive pentose phosphate cycle). In this cycle, three molecules of $CO_2$ are fed through a series of enzymatic reactions that generate a variety of phosphorylated compounds, which when coupled to glycolysis, produce a single molecule of acetyl-CoA.

Due in part to this ability to fix atmospheric carbon, a number of methods have been developed to divert the products of these reactions into commercially valuable materials such as alcohols, fuels, and biodegradable plastics. For example, WO 2009/098089 to Duhring et al. teaches certain genetic modifications of photosynthetic autotrophs to enhance activity or to modify cofactor specificity of enzymes involved in the production of specific metabolites, and to overexpress enzymes involved in ethanol synthesis from such metabolites. Similarly, US 2012/0142066 to Baier et al. teaches genetically engineered photoautotrophs to enhance ethanol production by overexpression of enzymes involved in the ethanol synthesis and reduction of activity of enzymes that utilize intermediates in the ethanol synthesis in alternate pathways. While at least somewhat effective, such methods are typically limited to ethanol production and, in addition, fail to address issues of inefficient fixation of $CO_2$.

More recently, an improved $CO_2$ fixation process was reported where a non-oxidative glycolysis (NOG) step used three molecules of fructose-6-phosphate to produce three molecules of acetyl-CoA, and where further carbon rearrangement reactions were needed to regenerate two molecules of fructose-6-phosphate (see e.g., Nature 502, 693-697 (31 Oct. 2013)). Thus, one molecule of 'surplus' fructose-6-phosphate from the CBB cycle was used to form three molecules of acetyl-CoA, and six molecules of $CO_2$ were needed to obtain via glyceraldehyde-3-phosphate the fructose-6-phosphate. Therefore, viewed from a different perspective, the NOG pathway required a transaldolase key step (C6+C4→C3+C7) and subsequent conversion of glyceraldehyde-3-phosphate to fructose-6-phosphate before the fructose-6-phosphate enters the non-oxidative glycolysis. However, while at least somewhat improving $CO_2$ fixation, additional genetic modifications were required to absorb and reconfigure the erythrose-4-phosphate byproduct from the acetyl-CoA generation and to ultimately regenerate fructose-6-phosphate.

Regardless of the efficiency of $CO_2$ fixation, at least some of the microorganisms that produce value products (e.g., alcohols, polyhydroxyalkanoates, etc.) often require substantial quantities of nitrogen (typically in form of ammonia) to grow to a desirable cell density. Unfortunately, relatively high nitrogen levels favor cell growth over value production, and the cells are typically shifted to nitrogen-limiting or nitrogen depletion conditions to shift the cells to value product formation. However, low nitrogen levels in the growth medium have also been found to reduce the rate of $CO_2$ fixation, likely by feedback inhibition of a CBB cycle metabolite, limiting overall yield of the value products.

Thus, there is still a need for methods and compositions that permit efficient carbon fixation by autotrophic organisms under conditions that also permit efficient production of value added materials without imposing undue metabolic burden and additional catalytic activities onto a cell. Moreover, there is also a need to provide metabolically engineered cells that can produce value products at a high rate under nitrogen-limiting or nitrogen depletion conditions without feedback inhibition by a CBB cycle metabolite that accumulates under such conditions.

SUMMARY OF THE INVENTION

The inventive subject matter is drawn to various genetically engineered cells, systems, and methods of production of various value products from $CO_2$. In most preferred aspects of the inventive subject matter, a cell having a CBB cycle is genetically modified such that two molecules of $CO_2$ fixed in the CBB cycle can be drawn as a single C2 compound from the modified CBB cycle without the need for additional recombinant enzymatic activity/activities outside the already existing catalytic activities in the CBB cycle. Viewed from a different perspective it should be recognized that efficient C2 extraction from the CBB cycle can be achieved by only minimally modifying the enzymatic activities in the CBB cycle.

In addition, the inventors discovered that the so genetically engineered cells are also less prone (or even entirely insensitive) to feedback inhibition of $CO_2$ fixation in the CBB cycle via reduced phosphoenol pyruvate (PEP) accumulation. Therefore, high quantities of value product can be produced at high $CO_2$ fixation efficiency by extraction of C2 molecules from the CBB cycle without build-up of PEP. In contrast, an unmodified CBB cycle leads to formation of glyceraldehyde-3-phosphate and subsequently phosphoenolpyruvate (PEP), which was found to inhibit $CO_2$ fixation and therefore value product formation.

In one aspect of the inventive subject matter, a method for improving the efficiency of carbon dioxide fixation in an organism having a CBB cycle. Such methods will typically include a step of genetically modifying the organism to produce or overexpress a first enzyme with a phosphoketolase activity, and to produce or overexpress a second enzyme with a phosphoribulokinase activity. In most instances, the first enzyme utilizes an intermediate of the CBB pathway (e.g., fructose-6-phosphate) as a substrate and generates a first acetyl phosphate product, and the phosphoribulokinase activity is produced or overexpressed in an amount to achieve a phosphoribulokinase activity level that is higher than the native phosphoribulokinase activity level (i.e., before genetic modification) of the organism. It is further preferred that the first acetyl phosphate product is converted in the organism to acetyl-CoA.

In some aspects of the inventive subject matter, the genetically modified organism fixes $CO_2$ in a medium containing nitrogen (e.g., present as ammonium) in an amount of less than 3 mM. While not limiting to the inventive subject matter, it is also contemplated that the genetically modified organism is further modified to produce from the acetyl-CoA a value added product (e.g., an alcohol, a fuel, a plastic polymer, or monomers suitable for plastic polymer synthesis), and especially PHA, n-butanol, isobutanol, an alkene, or biodiesel.

In other aspects of the inventive subject matter, the production of PEP in the genetically modified organism is decreased relative to that of a non-modified organism of the same species, particularly under nitrogen limiting or nitrogen depletion conditions. Thus, it is contemplated that the production of PEP in the genetically modified organism, when grown under nitrogen depletion, is below a feedback inhibitory concentration for the CBB cycle. Moreover, it is typically preferred that the produced or overexpressed phosphoribulokinase activity is in an amount that is effective to avoid depletion of ribulose-5-phosphate in the CBB cycle by the phosphoketolase activity.

Therefore, and viewed from a different perspective, the inventors also contemplate a metabolically engineered cell having a native CBB cycle. Especially contemplated cells will include a recombinant nucleic acid comprising a nucleic acid sequence encoding a first enzyme with a phosphoketolase activity and a second enzyme with a phosphoribulokinase activity, wherein the first enzyme utilizes an intermediate of the CBB pathway as a substrate and generates a first acetyl phosphate product, and wherein the phosphoribulokinase activity is produced or overexpressed in an amount that avoids depletion of ribulose-5-phosphate in the CBB cycle. Most typically (but not necessarily), the metabolically engineered cell is a bacterial cell (e.g., belonging to the genus *Ralstonia*). Such cells may be characterized in that their production of PEP, when grown under nitrogen depletion, is below a feedback inhibitory concentration for the CBB cycle.

In further contemplated aspects of the inventive subject matter, the inventors also contemplate a method of reducing PEP in a CBB dependent microorganism under nitrogen limitation condition. Such methods will generally include a step of genetically modifying the microorganism to produce or overexpress a first enzyme with a phosphoketolase activity to thereby generate acetylphosphate from an intermediate of the CBB cycle, and another step of genetically modifying the organism with the CBB cycle to produce or overexpress a second enzyme with a phosphoribulokinase activity, wherein the phosphoribulokinase activity is produced or overexpressed in an amount to achieve a phosphoribulokinase activity level that is higher than the native phosphoribulokinase activity level of the organism. The microorganism is then used to withdraw the acetylphosphate from the CBB cycle via conversion of the acetylphosphate to acetyl-CoA (or downstream value product using acetyl-CoA) to so reduce availability of glyceraldehyde-3-phosphate for PEP formation.

Most typically, the nitrogen limitation condition is characterized by the presence of ammonium in an amount of less than 3 mM, and it is generally preferred that the nitrogen content in the growth medium is controlled such that PEP concentration within the organism is below 0.2 mM. While not limiting to the inventive subject matter, the microorganism is preferably grown in continuous fermentation. Among other suitable value products, various alcohols, biodiesel, alkenes, PHA, or monomers suitable for polymer synthesis are especially contemplated.

Additionally, it is contemplated that the intracellular concentration of PEP may be further reduced in such cells by overexpressing an enzyme with a pyruvate kinase activity to convert PEP to pyruvate. Moreover, and where desirable, the cell may be further genetically modified such that the cell has a decreased acetyl-CoA flux into the tricarboxylic acid cycle (TCA cycle), or decreased activities of one or multiple enzymes within the TCA cycle.

Therefore, the inventors also contemplate a method for producing a value added product in a microorganism having a CBB cycle (e.g., microorganism belonging to the genus of *Ralstonia*). Most preferably, such method will comprise a step of providing a genetically modified organism having a recombinant first enzyme with a phosphoketolase activity, and wherein the genetically modified organism overexpresses a second enzyme in the CBB cycle having an equilibrium constant of at least 1000. In most aspects, the genetically modified organism produces one molecule of acetyl-CoA through fixation of two molecules of carbon dioxide in the CBB cycle. In a further step, the genetically modified organism is cultured, optionally under low nitrogen conditions, while supplying a source of carbon dioxide, wherein the genetically modified organism uses the acetyl-CoA to produce a value added product (e.g., an alcohol, a fuel, a plastic polymer, or a monomer suitable for plastic polymer synthesis).

In further aspects of contemplated methods, the source of carbon dioxide may be a combustion product, a flue gas, a fermentation product, a $CO_2$ enriched gas, an at least partially purified $CO_2$ gas, a carbonate or bicarbonate solution, an organic acid, and/or formic acid. Moreover, it is contemplated that the step of culturing the genetically modified organism is performed by culturing the organism under nitrogen rich conditions prior to culturing the genetically modified organisms under low nitrogen conditions.

Various objects, features, aspects and advantages of the inventive subject matter will become more apparent from the following detailed description of preferred embodiments, along with the accompanying drawing figures in which like numerals represent like components.

DETAILED DESCRIPTION

The following description includes information that may be useful in understanding the present invention. It is not an admission that any of the information provided herein is prior art or relevant to the presently claimed invention, or that any publication specifically or implicitly referenced is prior art.

The inventors have discovered systems and methods for genetically engineered cells in which the CBB cycle of an autotrophic organism is altered to derive value-added products directly from a C2 body (e.g., acetyl-CoA) that is directly derived from the modified CBB cycle without the C2 body having been produced via a C3 body (e.g., phosphoenolpyruvate (PEP)). Thus, and viewed from a different perspective, value-added products can be obtained from $CO_2$ fixation into a C2 body while at least partially decoupling production of the value added product from PEP. Hence, it should be appreciated that various value-added products can be directly obtained from C2 bodies that are drawn from the CBB without a C1 loss from PEP, which increases the efficiency of $CO_2$ fixation into such value-added products.

Moreover, it should be especially appreciated that contemplated cells, systems, and methods advantageously avoid accumulation of PEP within the cell that would otherwise lead to a drastic reduction in production of various value products derived from acetyl-CoA, and particularly where the cell is cultured under nitrogen limitation (e.g., ≤1 mM $NH_4^+$). Indeed, the inventors also discovered that nutrient (and especially nitrogen) limitation leads to an accumulation of PEP within the cell that in turn leads to a reduced $CO_2$ fixation via the CBB cycle, and with that substantially decreased pyruvate/acetyl-CoA quantities that would otherwise be available for production of value products from $CO_2$ fixation. Viewed from a different perspective, it should be noted that genetically modified organisms contemplated herein produce one molecule of acetyl-CoA through the fixation of two molecules of $CO_2$ without losing fixed carbon as $CO_2$ in the process.

Figure 1:
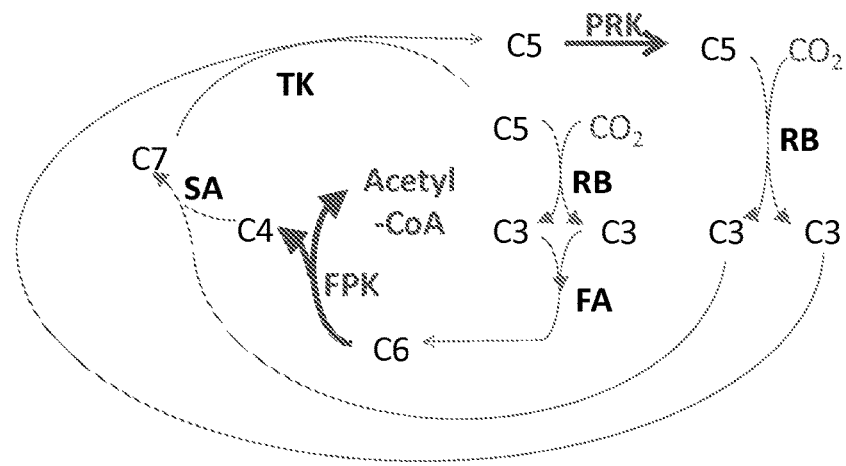
FIG. 1 depicts an exemplary simplified scheme of a modified CBB cycle according to the inventive subject matter.

This and other advantages can be accomplished by genetically modifying an organism that utilizes the CBB cycle to express an enzyme activity that utilizes fructose-6-phosphate as a substrate and generates acetylphosphate, an acetyl-CoA precursor, as a product. Among other suitable enzymes, enzymes with phosphoketolase activity are especially suitable as they will utilize fructose-6-phosphate as a substrate and produce acetylphosphate and erythrose-4-phosphate. However, enzymes expressing such activity frequently can also utilize xylulose-5-phosphate as a substrate and can therefore potentially deplete the CBB cycle of ribulose-5-phosphate utilized in $CO_2$ capture. Surprisingly, the inventors have found that this depletion can be avoided by engineering the autotrophic organism to overexpress enzymatic activity that utilizes ribulose-5-phosphate as a substrate to produce ribulose-1,5-diphosphate as is exemplarily and schematically illustrated in the simplified scheme for the modified CBB cycle of FIG. 1. Here, the overall reaction for CO2 fixation into the CBB cycle follows the equation 2 CO2+6 ATP+4 NADPH→1 Acetyl-CoA. In FIG. 1, FA is fructose-1,6-bisphosphate, SA is sedoheptulose-1,7-bisphosphate aldolase, TK is transketolase, PRK is phosphoribulokinase, FPK is F6P phosphoketolase, and RB is RuBisCo. As can be readily seen, two C1 molecules ($CO_2$) are fixed onto two C5 molecules (ribulose-1,5-bisphosphate) and the reaction products are then turned over in the engineered CBB pathway to produce one C2 molecule (acetyl-CoA) and a byproduct that forms part of the CBB cycle.

In that context, it should be noted that incorporation of two C1 molecules of $CO_2$ is accompanied by the formation of a product that leads to acetyl-CoA (and hence to value added products) through the F6P activity of phosphoketolase, via a metabolic pathway that does not lead to down-regulation of the CBB cycle as a substantial amount of carbon entering the CBB cycle is withdrawn as a C2 product (acetylphosphate) as opposed to a C3 product (glyceraldehydes-3-phosphate) that would otherwise require transformation to acetyl-CoA (e.g., via oxidative decarboxylation). For example, acetylphosphate can be converted to acetyl-CoA phosphotransacetylase or phophate acyl transferase (EC 2.3.1.8; which may be native to a cell or be recombinant). It should be noted, however, that the C3 products produced through $CO_2$ fixation by RuBisCo during the process can also lead to at least some degree to acetyl-CoA (and hence to value added products). Inventors therefore believe that the increased carbon fixation efficiency can result in improved growth and production of value added products (for example alcohols, biofuels, PHA, monomers suitable for use in plastic production, and/or plastic polymers) in autotrophs with such a modified CBB cycles.

Figure 2:
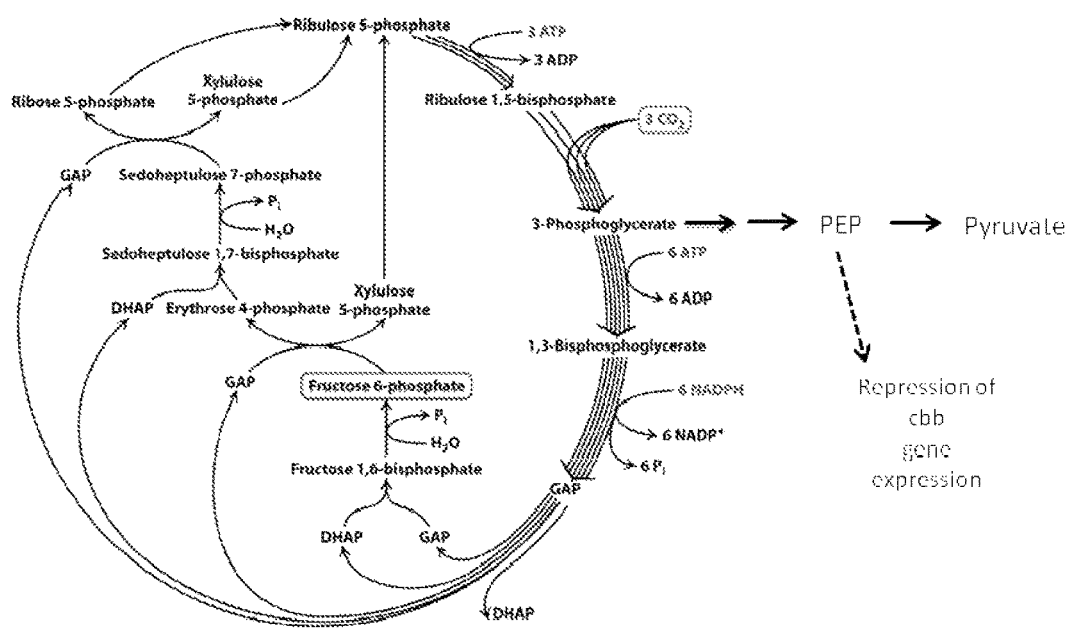
FIG. 2 is a more detailed scheme of an unmodified CBB cycle and PEP production therefrom.

FIG. 2 illustrates a more detailed view of an unmodified CBB cycle in which $CO_2$ is fixed by RuBisCo (not shown) utilizing ribulose-1,5-biphosphate to produce 3-phosphoglycerate, a precursor to PEP and pyruvate used in the synthesis of value added compounds. When coupled with glycolysis, the overall $CO_2$ fixation reaction follows the equation: 3 CO2+7 ATP+4 NADPH→Acetyl-CoA. With further reference to FIG. 2 it should be noted that the CBB cycle utilizes xylulose-5-phosphate in the generation of ribulose-5-phosphate that is then further phosphorylated by a ribulokinase to finally form the $CO_2$ acceptor ribulose-1,5-bisphosphate. As noted above, addition of recombinant phosphoketolase will advantageously produce a C2-compound plus erythrose-4-phosphate. Unfortunately, the phosphoketolase can also utilize compounds other than fructose 6-phosphate as substrates, and particularly xylulose-5-phosphate leading to depletion of ribulose-5-phosphate, which in turn depletes ribulose-1,5-bisphosphate. This activity can thus have the undesirable effect of reducing $CO_2$ fixation.

The inventors have now discovered that the adverse effect of undesirable xylulose-5-phosphate activity of the recombinant phosphoketolase can be reduced or even eliminated through overexpression of phosphoribulokinase having an enzymatic activity that is already present in the CBB cycle (catalyzing formation of ribulose-1,5-bisphosphate from ribulose-5-phosphate). As used herein, 'overexpression" of a gene means expression of that gene to form a gene product in an amount such that the amount is greater than zero or in an amount that is greater than an amount that would otherwise be already present in the cell without the overexpression.

Figure 3:
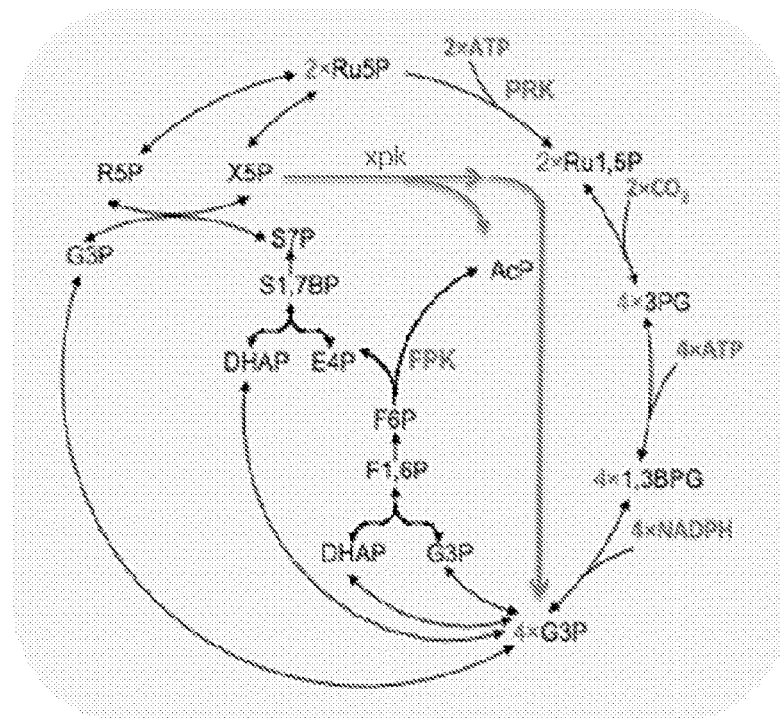
FIG. 3 depicts an exemplary simplified schematic of a modified CBB cycle showing catalytic activity of FPK on xylulose-5-phosphate.

As can be seen in FIG. 2, xylulose-5-phosphate is in an equilibrium with ribose 5-phosphate. However, in a practical sense, ribulose-5-phosphate is clearly not in equilibrium with ribulose-1,5-bisphosphate as the conversion of ATP to ADP in that reaction provides a significant barrier to the reverse reaction. Indeed, phosphoribulokinase could be considered to have an equilibrium constant of at least 1000, and as such to catalyze the formation of ribulose-1,5-bisphosphate in an almost unidirectional manner. Consequently, it should be appreciated that overexpression of phosphoribulokinase will result in depletion of ribulose-5-phosphate, which in turn leads to depletion of ribose 5-phosphate. This depletion of ribose 5-phosphate shifts the equilibrium between ribose-5-phosphate and xylulose 5-phosphate, and therefore reduces the amount of xylulose-5-phosphate available to act as a substrate for phosphoketolase, effectively reducing this activity (i.e., through substrate competition) while not impacting the production of ribulose 1,5-bisphosphate necessary for $CO_2$ fixation. Thus, overexpression of phosphoribulokinase will substantially irreversibly drain ribulose-5-phosphate to ribulose-1,5-bisphosphate to thereby keep xylulose-5-phosphate low. Viewed from a different perspective, the reaction sequence to regenerate ribulose 1,5-bisphosphate is therefore 'pulled' through ribose-5-phosphate to ribulose-5-phosphate rather than through xylulose 5-phosphate. FIG. 3 depicts a simplified schematic of a modified CBB cycle with no overexpression of phosphoribulokinase illustrating the effect of the phosphoketolase on fructose-6-phosphate (FRK) and xylulose-5-phosphate (XPK).

Of course, it should be appreciated that the overexpression of the phosphoribulokinase could also be replaced or supplemented by native or recombinant expression of a mutant form of phosphoribulokinase that exhibits a substrate specificity towards fructose-6-phosphate. For example, suitable mutant forms will have a substrate specificity of fructose-6-phosphate versus xylulose-5-phosphate (e.g., as measured by $K_m$) of at least 5:1, more preferably at least 10:1, even more preferably at least 100:1, and most preferably at least 500:1.

Therefore, an alternate and stable CBB pathway is provided that utilizes the fixation of two molecules of $CO_2$ to produce 1 molecule of acetyl-CoA, compared to three molecules of $CO_2$ via the native CBB cycle, thereby improving the efficiency of $CO_2$ conversion into value-added products otherwise derived from PEP (and/or other C2 metabolites derived from the CBB cycle) at least conceptually from 66% to 100%. The recitation of ranges of values herein is merely intended to serve as a shorthand method of referring individually to each separate value falling within the range. Unless otherwise indicated herein, each individual value is incorporated into the specification as if it were individually recited herein.

Phosphoketolase, EC 4.1.2.9, can be found in numerous sources, and cloning and stable or transient expression will follow generally well-known laboratory protocols using appropriate vectors. For example, phosphoketolase is known from *Lactobacillus* (see e.g., *J Microbiol Biotechnol.* 2007 May; 17(5):822-9), *Bifidobacterium breve* (see e.g., *BMC Genomics.* 2014 Mar. 1; 15:170), *Bifidobacterium adolescentis* (see e.g., *Appl Microbiol Biotechnol.* 2009 July; 83(6):1115-26), *Acetobacter xylinum* (see e.g., *J Biol Chem.* 1958 December; 233(6):1283-8), *Bifidobacterium longum* (see e.g., *Lett Appl Microbiol.* 2001 April; 32(4):235-9), etc. Likewise, phosphoribulokinase EC 2.7.1.19 is well known and can be cloned from numerous sources, and cloning and stable or transient expression will follow generally well-known laboratory protocols using appropriate vectors. For example, phosphoribulokinase can be cloned from *Arabidopsis thaliana* (see e.g., *J Exp Bot.* 2005 January; 56(409): 73-80), *Rhodobacter sphaeroides* (see e.g., *Protein Sci.* 2006 April; 15(4):837-42), etc. In some embodiments of the inventive concept, it is contemplated that the overexpression can reduce the apparent xylulose-5 phosphate activity of a phosphoketolase by at least 50%, or by at least 60%, or at least 70% relative to the activity observed in a similar organism that does not overexpress phosphoribulokinase.

In a still further notable aspect of the inventive subject matter, withdrawal of the fixed $CO_2$ via C2 compounds form the CBB cycle has a further benefit in avoiding accumulation of PEP in the cell to a level that would otherwise inhibit CO2 fixation in the CBB cycle. Thus, not only is $CO_2$ fixation more effective, but can also lead to higher cell densities and yield for value products produced from acetyl-CoA. In other words, the inventors have surprisingly discovered that the CBB cycle can also be modified to reduce or even eliminate the effect of nitrogen depletion on carbon fixation as is described in more detail below.

Production of value added products by microorganisms capable of fixing carbon is typically performed in culture, with the provision of various nutrients as necessary to support growth and metabolism of autotrophic organisms. Such nutrients include nitrogen, often in the form of ammonia or an ammonium salt. The concentration of such nutrients can be controlled in order to modulate the growth and/or metabolic state of the cultured autotrophs. For example, nitrogen in the form of an ammonium salt can be provided at nitrogen depletion concentrations (i.e., 1 mM $NH_4^+$ or less), low nitrogen concentrations (i.e., from 2 mM to 4 mM $NH_4^+$), and nitrogen rich (e.g., ≥10 mM $NH_4^+$). Nitrogen rich conditions can support rapid growth and accumulation of biomass of the microorganism, but may not be ideal for production of value added products as most of the nutrients are fed to oxidative glycolysis. On the other hand, nitrogen depletion conditions may not support growth of cultured microorganisms but can increase the production of value added products.

Figure 4:
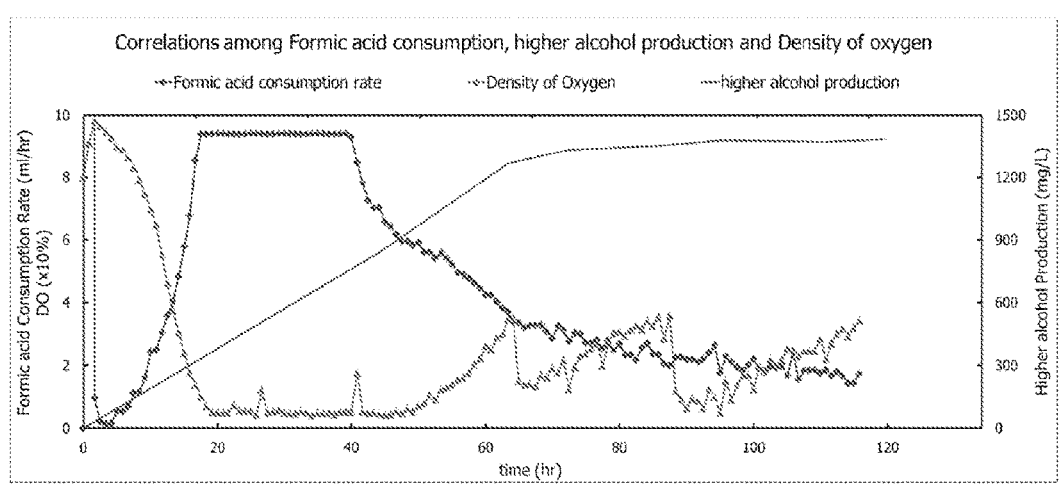
FIG. 4 is a graph depicting exemplary test results in which $CO_2$ fixation (provided as formic acid) and alcohol production is inversely dependent on nitrogen levels.

This phenomenon can be exploited to improve the efficiency of the production of, for example, alcohols by initially providing a nitrogen rich environment to grow the autotrophs to the desired density then reducing the nitrogen concentration in the culture media to nitrogen depletion conditions. Results of such a process are shown in FIG. 4, in which cells were grown at 15 mM $NH_4^+$ for 32 hours, at which point the concentration of $NH_4^+$ was reduced to less than 1 mM. In this instance $CO_2$ was provided in the form of formic acid and the value added product produced was a higher alcohol (for example, isobutanol). While this approach enhances production of the value added product to at least some degree, it can also be clearly seen that the fixation of $CO_2$ in the form of formic acid decreases dramatically shortly after nitrogen depletion conditions are established. Such decrease is undesirable as this decrease in carbon fixation limits the capacity for synthesis of value added products.

Figure 5:
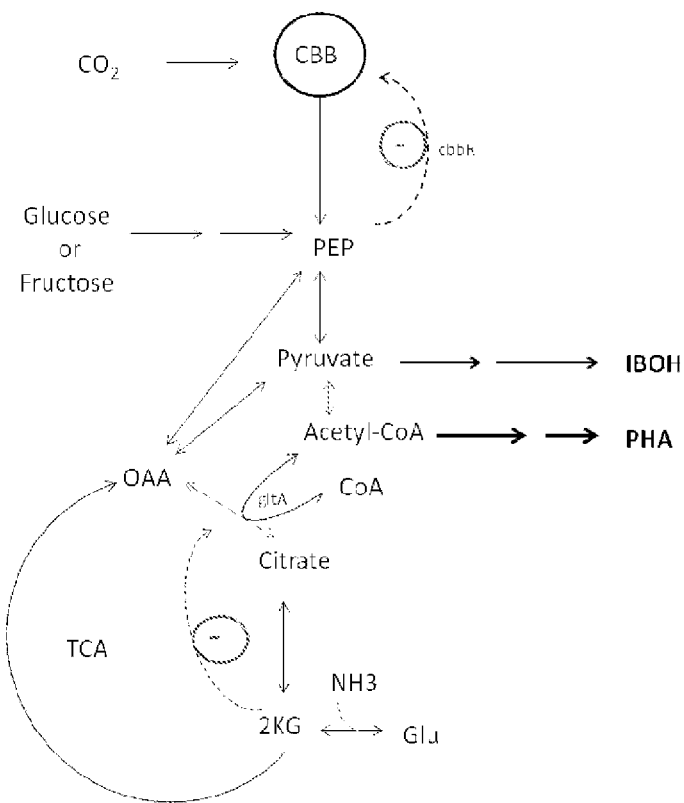
FIG. 5 is a schematic of metabolic pathways illustrating inhibition of the CBB cycle by PEP under nitrogen depletion.

Without wishing to be bound by any theory or hypothesis, the inventors believe that such decrease is due, at least in part, to the accumulation of C3-precursors of the value added products, and especially PEP. One mechanism by which this can occur is shown in FIG. 5. As can be seen in FIG. 5, $CO_2$ fixation in an unmodified CBB cycle (CBB) results in the production of phosphoenolpyruvate (PEP), which can be utilized in the synthesis of added value products isobutanol (IBOH) and PHA via pyruvate and Acetyl-CoA, respectively. PEP is also in equilibrium with oxaloacetate produced as part of the citric acid cycle. Nitrogen depletion conditions can lead to an accumulation of alpha-ketoglutarate (2 KG) produced in the citric acid cycle through decreased synthesis of glutamic acid. This can, in turn, lead to elevated concentrations of oxaloacetic acid, which leads to increased production of PEP via the equilibrium reaction. Since PEP can down-regulate enzymes of CBB cycle (PEP-cBBR inhibits PcbbL promoter, which express the cbbL operon; the cbbL operon encodes the Rubisco large subunit and Rubisco small subunit 2), nitrogen depletion conditions can result in decreased carbon fixation via the CBB cycle. Therefore, a paradoxical situation will arise in which the same conditions that favor production of value products from $CO_2$ fixation over cell growth (i.e., low nitrogen levels) are also material in the throttling down of the CBB cycle that is used to generate the value products.

Figure 6:
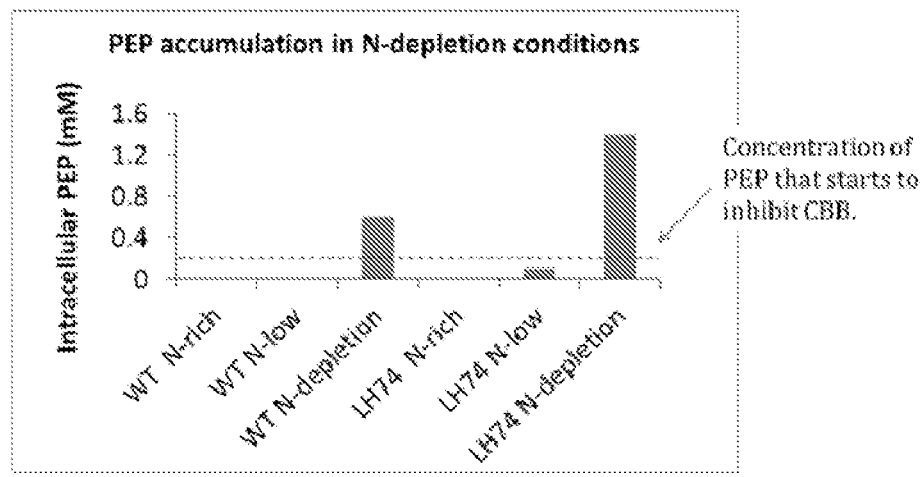
FIG. 6 is a graph depicting accumulation of intracellular phosphoenolpyruvate (PEP) under various nitrogen depletion conditions.

FIG. 6 exemplarily depicts intracellular PEP concentration as a function of nitrogen levels in the growth medium for two *Ralstonia* strains (WT: wildtype; LH44N: isobutanol production strain with deleted PHA production pathway) without modified CBB cycle. Both strains were grown under nitrogen rich (N-rich: $NH4^+$>10 mM), low nitrogen (N-low: $NH4^+$ approximately 3 mM in continuous run), and nitrogen depletion (N-depletion: $NH4^+$<1 mM) conditions. Also indicated by the dashed line is the threshold where inhibition of the CBB cycle by PEP was experimentally observed. Here, the observed increase in intracellular PEP is consistent with concentrations necessary for down-regulation of CBB cycle enzymes, which in turn is consistent with the observed loss of carbon fixation under nitrogen depletion conditions.

Therefore, the inventors also contemplate growth and production conditions for cells having a CBB cycle (which may be modified as described above or unmodified) in which the intracellular concentration of PEP is maintained below threshold of about 0.2 mM. In most cases, this can be achieved by maintaining the ammonia concentration in the medium at a level of about 3 mM or below, which may be advantageously achieved using a continuous fermentation protocol.

Figure 7:
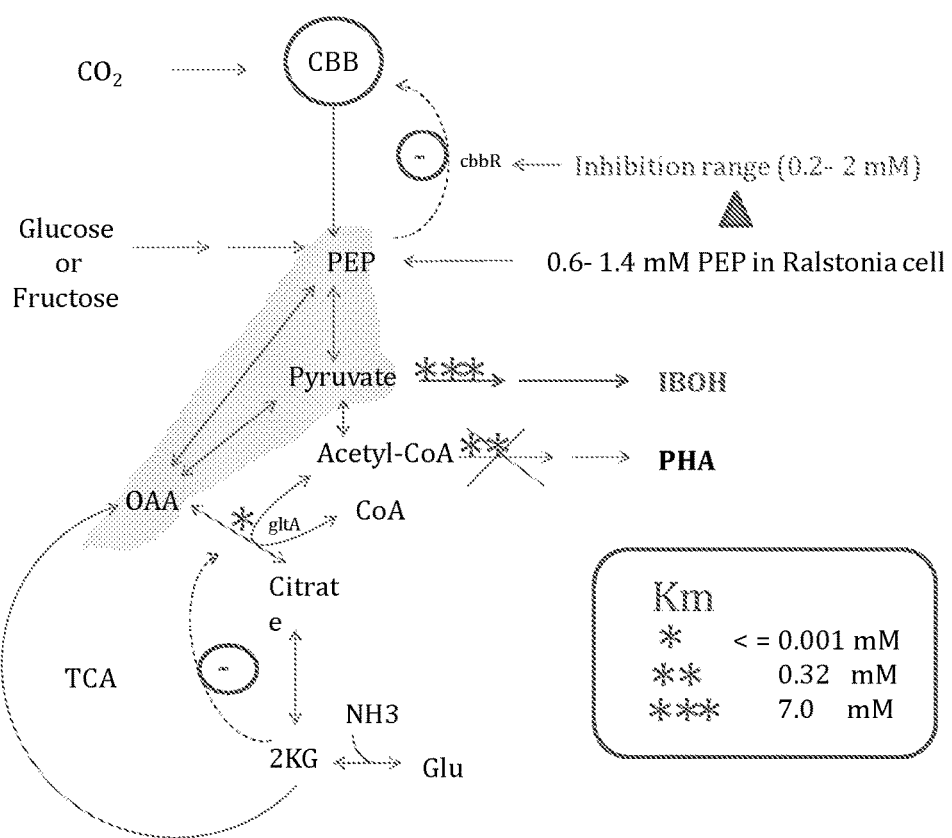
FIG. 7 is another schematic of metabolic pathways illustrating inhibition of the CBB cycle by PEP under nitrogen depletion.

As already noted above and further illustrated in FIG. 7, the accumulation of PEP could be explained by the hypothesis that the nitrogen limitation induced shutdown of TCA cycle could further increase intracellular concentration of OAA and acetyl-CoA, and eventually pyruvate and PEP, since there is no PHA production pathway in the engineered *R.eutropha* strain LH47N. The inhibition of CBB could stop the fixation of $CO_2$ and the formate consumption, therefore ceasing the isobutanol production. It needs to be highlighted that PEP does not affect the consumption of fructose because the glycolysis is not inhibited by PEP. Therefore, the nitrogen limitation induced PEP accumulation does not affect the production of isobutanol from fructose. This result sheds new light on the observation that the production strains could produce isobutanol efficiently from fructose, but not from formate.

Figure 8:
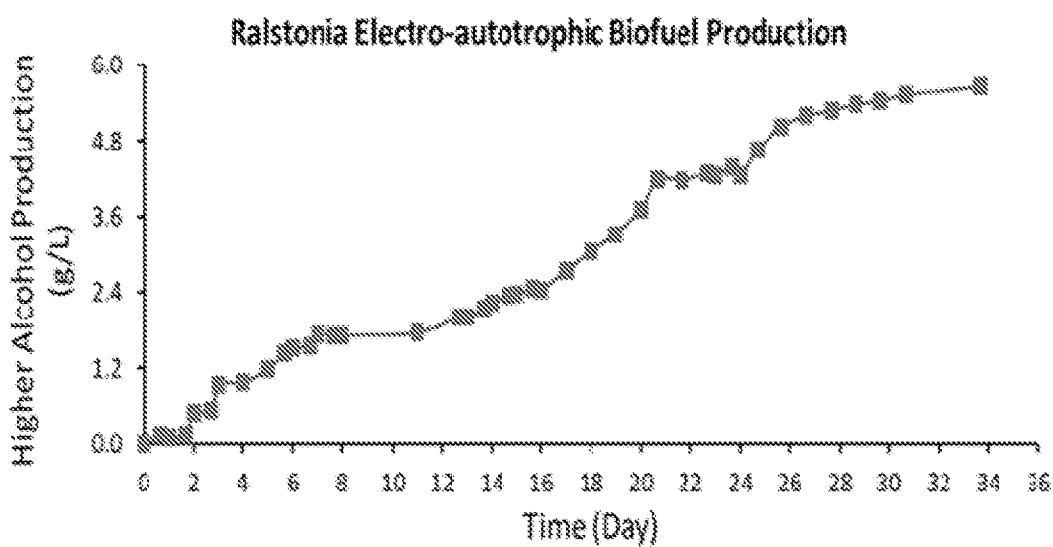
FIG. 8 is a graph illustrating increased electro-autotrophic biofuel production under nitrogen level control to avoid feedback inhibition by PEP.

Taken together, the engineered production *Ralstonia* has an AlsS protein to convert pyruvate to acetolactate for isobutanol production. The AlsS's Km value for pyruvate is 7 mM. Therefore, AlsS could only efficiently consume pyruvate when pyruvate concentrations are relatively high. However, high pyruvate concentrations will induce PEP accumulation. To solve this problem without modificaiton of the CBB cycle, the inventors used a continuous fermentation process during which the chemical environment inside the fermentor is static (chemostat). Fresh medium was continuously added, while culture liquid was continuously removed to keep the culture volume constant. By changing the rate with which medium is added to the bioreactor, the growth rate of the microorganism can be controlled. During the fermentation process, the concentration of ammonium in the broth was maintained around 3 mM. The EB-074 cells grown in N-limitation medium had intracellular PEP concentrations less than 0.1 mM. That is to say, EB-074 did not accumulate a significant amount of PEP inside the cells under continuous fermentation conditions when formate was used as the sole carbon source. Formate consumption and formate concentration in the fermentation vessel were stable during the 34 day run as well. As can be seen from FIG. 8, the maximum captured electro-autotrophic biofuel reached 5.6 g/L under continuous fermentation with continuous feeding of $(NH_4)_2SO_4$ so that its concentration is around 200 mg/L (3 mM $NH4^+$). This resulted in low nitrogen conditions, which avoid PEP accumulation, and which in turn avoids CBB inhibition, resulting in continuous high level production.

It should be recognized that the production conditions could also be performed with cells having a modified CBB cycle as descibed above as such cycle advantageously also at least partially decouples the synthesis of value added products from the generation of PEP. This decoupling can reduce or eliminate the need to generate high concentrations of PEP and the subsequent down-regulation of cbb gene expression.

Modification of the CBB cycle in a microorganism were performed following standard recombinant cloning protocols known in the art. In one exemplary and typical modification, plasmids for expressing Phosphoketolase (F/XPK) and phosphoribulokinase (PRK) were constructed using pQE9 (Qiagen) as the vector backbone. The expression of F/Xpk and PRK in their corresponding plasmids in *Ralstonia* were under the control of the PLlacO1 promoter. The genomic template for F/Xpk was from *B. adolescentis* ATCC 15703, and the genomic template for PRK was from *Synechocystis* sp. PCC 6803 Improved acetyl-CoA/value product formation in the so modified *Ralstonia* was observed using standard techniques.

The conjugation and transformation methods were used as the genetic tool to alter the pathway in *Ralstonia*. The wild-type PHB biosynthesis genes in the *Ralstonia* production strain were knocked out by chromosomal replacement while a chloramphenicol acetyltransferase (CAT) cassette was inserted. *E.coli* genomic DNA was used to clone the plasmid containing alsS, ilvC, and ilvD genes. The purified plasmid was transformed into an *E.coli* conjugation strain (referred to as the donor strain). The donor strain containing the desired plasmid and the recipient *Ralstonia* strain are incubated together on an agar plate. The alsS-ilvC-ilvD operon was transferred from the donor to the chromosome of the recipient *Ralstonia* strain via double crossover. To produce isobutanol, the kivd-yqhD operon was constructed into a plasmid which was introduced into the above *Rasltonia* strain through transformation. The genes kivd and yqhD were purified from *Lactococcus lactis* and *E. coli* genomic DNA, respectively. The yqhD gene was chosen to be the alcohol dehydrogenase because it is NADPH dependent and there is an abundant NADPH supply in the cell.

To test the performance of the engineered *Ralstonia* production strain, formate-based autotrophic bench-scale fermentations were performed. The formate-based fermentation used 1.8 L J minimal medium cultured with the production strain in a 5 L fermentor J minimal medium contains 1 g/L $(NH4)_2SO_4$, 0.5 g/L $KH_2PO_4$, 6.8 g/L $NaHPO_4$, 4 mg/L $CaSO_4$-$2H_2O$, 100 ug/l thiamine hydrochloride, 0.2 g/L $MgSO_4$-$7H_2O$, 20 mg/L $FeSO_4$-$7H_2O$, and 1 ml/L SL7 metals solution (SL7 metal solution contains 1% v/v 5M HCl (aq), 0.1 g/L $MnCl_2\text{-}4H_2O$, 1.5 g/L $FeCl_2\text{-}4H_2O$, 0.19 g/L $CoCl_2\text{-}6H_2O$, 0.036 g/L $Na_2MoO_4\text{-}2H_2O$, 0.07 g/L $ZnCl_2$, 0.062 g/L $H_3BO_3$, 0.025 g/L $NiCl_2\text{-}6H_2O$, and 0.017 g/L $CuCl_2\text{-}2H_2O$). Agitation, temperature, pH, and dissolved oxygen content (DO), air flow % and O2 flow % set points were held at 300 rpm, 30° C., 7.2, 5%, 100%, and 0%, respectively. Gas flow was controlled using a dynamic-control cascade that varied the gas flow rate based on the DO reading. Formic acid was added in small increments to prevent the protonated acid molecules from penetrating the cell membrane and acidifying the cytoplasm. The formic acid feed rate was coupled to changes in pH. A pH-driven cascade controller pumps in formic acid when the pH levels are elevated. This replenishes carbon levels as the formate is consumed by the cells. Graham condenser was used to collect the evaporated alcohols from gas vented from the fermentor. Every 24 hours, samples of culture broth and liquid condensed from the vented gas were collected, characterized, and quantified using gas chromatography (GC).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As also used in the description herein and throughout the claims that follow, the meaning of "a," "an," and "the" includes plural reference unless the context clearly dictates otherwise. Likewise, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

What is claimed is:

1. A method for improving the efficiency of carbon dioxide fixation in an organism having a Calvin-Benson-Bassham (CBB) cycle, comprising:
   genetically modifying the organism having the CBB cycle to produce or overexpress a first enzyme, and to produce or overexpress a second enzyme;
   wherein the first enzyme is phosphoketolase enzyme, belonging to EC 4.1.2.9 and the second enzyme is phosphoribulokinase enzyme belonging to EC 2.7.1.19;
   wherein the first enzyme utilizes an intermediate of the CBB pathway as a substrate and generates a first acetyl phosphate product;
   wherein the phosphoribulokinase enzyme is produced or overexpressed in an amount to achieve a phosphoribulokinase activity level that is higher than the native phosphoribulokinase activity level of the organism;
   wherein the second enzyme is overexpressed in the genetically modified organism in an amount to achieve a phosphoribulokinase activity level that is higher than the native phosphoribulokinase activity level of the organism, and the second enzyme utilizes ribulose-5-phosphate to produce ribulose-1,5-bisphosphate;
   wherein the first acetyl phosphate product is converted in the organism to acetyl-CoA;
   wherein the genetically modified organism fixes two $CO_2$ molecules onto two of the ribulose-1,5-bisphosphate molecules, and the reaction products are then turned over in the CBB cycle to produce one acetyl-CoA molecule from the first acetyl phosphate, when the organism is grown in culture at ammonium levels of less than 3 mM; and
   wherein the production of phosphoenolpyruvate (PEP) in the genetically modified organism, when grown under nitrogen depletion, is below a feedback inhibitory concentration for the CBB cycle.

2. The method of claim 1, wherein the intermediate of the CBB pathway is fructose-6-phosphate.

3. The method of claim 1, wherein the genetically modified organism fixes $CO_2$ in a medium containing nitrogen in an amount of less than 3 mM.

4. The method of claim 1, wherein the genetically modified organism is further modified to produce from the acetyl-CoA a value added product selected from the group consisting of an alcohol, a fuel, a plastic polymer, and a monomer suitable for plastic polymer synthesis.

5. The method of claim 1, wherein the genetically modified organism is further modified to produce from the acetyl-CoA a value added product selected from the group consisting of PHA, n-butanol, isobutanol, an alkene, and biodiesel.

6. The method of claim 1, wherein the production of phosphoenolpyruvate in the genetically modified organism is decreased relative to that of a non-modified organism of the same species.

7. The method of claim 1, wherein the genetically modified organism is a microorganism transformed with a pQ9 plasmid expressing a gene encoding phosphoketolase (F/XPK) and a pQ9 plasmid expressing a gene encoding phosphoribulokinase (PRK), wherein F/XPK is under the control of the PLlacO1 promoter.

8. The method of claim 7, wherein the genetically modified microorganism is further modified by inserting one or more additional plasmids into the modified microorganism, wherein the one or more additional plasmids comprise:
   a plasmid comprising an alsS, ilvC, and ilvD operon; and
   a plasmid comprising a kivd-yqhD operon.

9. The method of claim 7, wherein expression of the wild-type polyhydroxybutyrate (PHB) gene(s) is knocked out in the genetically modified microorganism.

10. The method of claim 7, wherein the F/Xpk gene was obtained from *B. adolescentis* ATCC 15703, and the PRK gene was obtained from *Synechocystis* sp. PCC 6803.

11. The method of claim 1, wherein the genetically modified organism is a microorganism that belongs to the genus of *Ralstonia*.

* * * * *